United States Patent [19]
Kolloff

[11] Patent Number: 4,464,925
[45] Date of Patent: Aug. 14, 1984

[54] HYDROGEN, DEUTERIUM THERMAL CONDUCTIVITY DETECTOR

[75] Inventor: Richard H. Kolloff, West Chester, Pa.

[73] Assignee: Hewlett-Packard Company, Palo Alto, Calif.

[21] Appl. No.: 378,662

[22] Filed: May 17, 1982

[51] Int. Cl.³ .............................................. G01N 31/08
[52] U.S. Cl. ..................................... 73/23.1; 73/27 R
[58] Field of Search ............................. 73/23.1, 27 R

[56] References Cited

U.S. PATENT DOCUMENTS

| | | | |
|---|---|---|---|
| 3,319,458 | 5/1967 | Curren | 73/23.1 |
| 3,537,914 | 11/1970 | Cieplinski et al. | 73/27 R |
| 4,170,126 | 10/1979 | Craven | 73/27 R |
| 4,185,490 | 1/1980 | Clouser et al. | 73/27 R |
| 4,254,654 | 3/1981 | Clouser et al. | 73/27 R |

Primary Examiner—Stephen A. Kreitman
Attorney, Agent, or Firm—Donald N. Timbie

[57] ABSTRACT

A thermal conductivity detector is described in which the temperature of the filament and wall are such as to cause the output signal to be on one side of zero for all mixtures of hydrogen or deuterium in a carrier gas such as helium.

12 Claims, 8 Drawing Figures

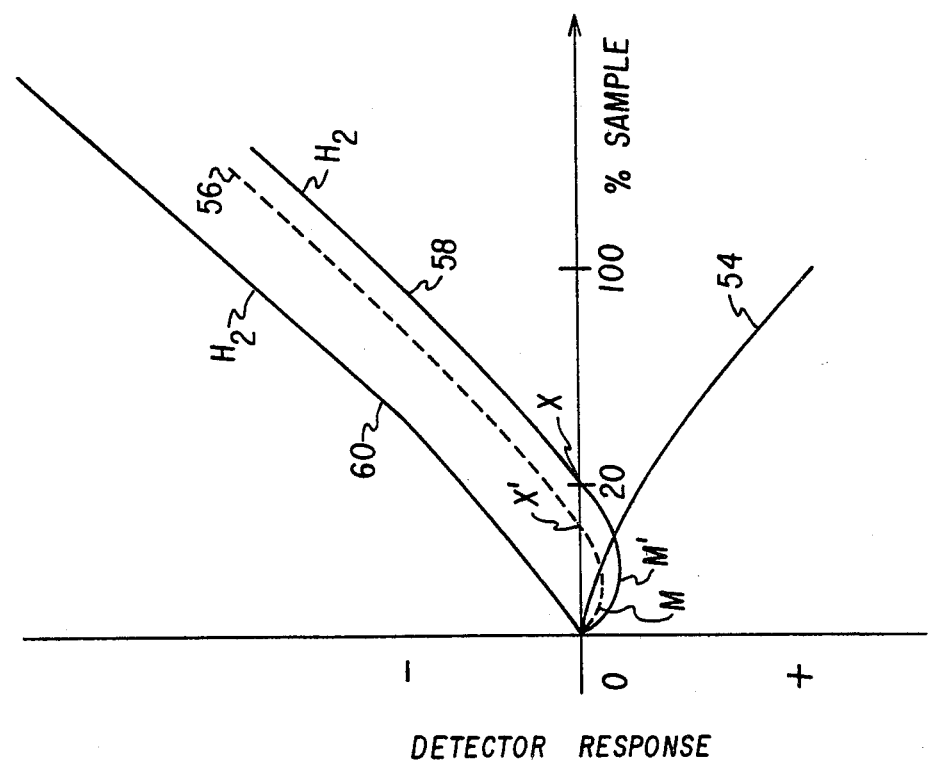

HYDROGEN, DEUTERIUM THERMAL CONDUCTIVITY DETECTOR

BACKGROUND OF THE INVENTION

Measurement of the relative amounts of gas contained in a sample mixture is often made by a gas chromatograph which includes means for causing a stream of carrier gas to flow through a column and a detector in sequence and means for injecting a known quantity of the mixture of gases to be quantified into the stream of carrier gas just before it enters the column. Ideally, each gas in the sample emerges from the column at different times so that, at any one time, the gas flowing into the detector is either all carrier gas or a combination of carrier gas and one of the gases of the sample mixture. The detector functions by producing a signal related to the change in the intensity of a given characteristic of the gases flowing through it. The intensity of the characteristic of the carrier gas is generally either greater or less than the intensity of the same characteristic of the gases in the sample mixture. Thus, as each sample gas passes through the detector, the output signal varies from the value it has when the detector is full of carrier gas, the amount of variation depending on the concentration of the sample gas.

One of the most widely used detectors is the thermal conductivity detector. It is comprised of a block having a cavity within it, a filament suspended in the cavity and ports at either end of the filament, one of which is connected to the end of the column from which the gases are eluting. Current is passed through the filament so as to heat it, and means are generally provided for maintaining the block and therefore the walls of the cavity at a fixed temperature that is less than the temperature of the filament. The output signal of the detector corresponds to the variation in voltage applied to the filament or the current flowing through it that are required to keep the filament at a given temperature or resistance. The temperature of the filament depends on the rate at which heat can flow from it to the walls of the cavity. Nearly all of the heat flows by conduction through the gases between the filament and the walls of the cavity. Because of its inertness and the fact that its thermal conductivity is greater than that of all gases except hydrogen, helium is generally used as a carrier gas.

Measuring the relative amount of hydrogen in a sample mixture is very difficult if helium is used as the carrier gas because the thermal conductivity of hydrogen is only slightly greater than that of helium, and also because the thermal conductivity of a mixture of hydrogen and helium decreases as the percentage of hydrogen in helium is gradually increased, rather than increasing as might be expected. After reaching a minimum value, the thermal conductivity of the mixture increases so as to pass through the thermal conductivity of helium alone so that only percentages of hydrogen less than that producing the minimum thermal conductivity can be measured. Depending on the temperature involved, the minimum thermal conductivity occurs at a very low percentage of hydrogen, usually less than 15%. Thus, if a sample mixture contains too much hydrogen, it must be diluted sufficiently to make the percentage of hydrogen in helium less than that which produces the minimum thermal conductivity of the mixture. A chromatogram representing hydrogen is on the opposite (−) side of the baseline from the chromatogram for other gases. Similar phenomena occur in measuring the relative amount of deuterium when helium is used as the carrier gas.

Another factor that interferes with the measurement just described in catalytic disassociation of hydrogen that takes place on the surface of the filament, i.e., the formation of two atoms H for each hydrogen molecule. Because this is an endothermic process, it draws heat from the filament so as to cause an error in the signal produced by the detector. Whereas these errors are small, it must be remembered that the signal is also small. Further difficulty arises from the fact that the error varies in such manner as to make compensation impossible.

The usual way of avoiding these difficulties is to employ a separate injector, column and detector for measuring hydrogen and using nitrogen or argon as the carrier gas. Because the thermal conductivity of the hydrogen is significantly different from either nitrogen or argon, the sensitivity is increased, thus reducing but not eliminating the errors introduced by catalytic disassociation. Of greater importance, however, is the fact that the thermal conductivity of the mixture of hydrogen and either nitrogen or argon increases with the percentage of hydrogen so that there is no minimum value as previously described.

BRIEF DESCRIPTION OF THE INVENTION

In accordance with the invention, the relative amounts of a mixture of gases including hydrogen can all be measured with a single injector, column and detector having helium as a carrier gas. This is accomplished by establishing the temperature of the filament and of the block at higher values than those normally used so that the thermal conductivity of the hydrogen and helium increases as the percentage of hydrogen increases. Because some thermal conductivity detectors have a greater volume between the filament and the wall of the cavity than others, the temperature to be employed will vary, but with any detector, the proper temperatures can be attained by adjusting the temperature of the filament and block until the chromatograms for all concentrations of hydrogen are on one side of the baseline.

In order to stabilize the measurements of small percentages of hydrogen in the stream of helium, the filament is coated with sufficient oxide to cover all the sites where catalytic disassociation can occur. Normally, this requires an oxide coating that is at least $10 \times 10^{-6}$ inches thick.

BRIEF DESCRIPTION OF THE DRAWINGS

FIG. 2 includes graphs representing the thermal conductivity of mixtures of carrier and sample gas as a function of the percentage of sample gas;

FIGS. 3A through 3D illustrate chromatograms produced by the prior art; and

FIG. 3E illustrates a chromatogram produced by use of this invention.

DETAILED DESCRIPTION OF THE INVENTION

Figure 1:
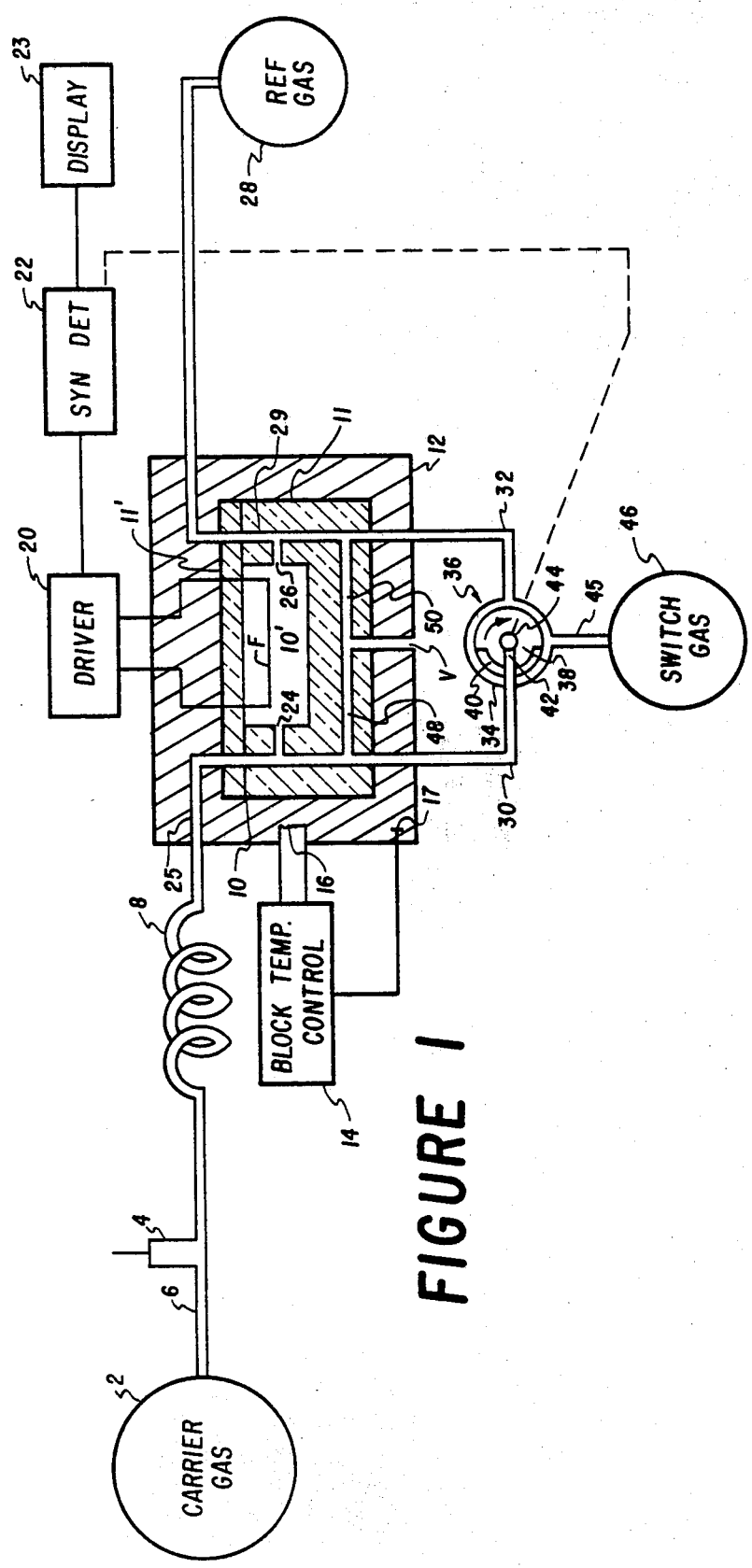
FIG. 1 is a schematic representation of a chromatograph that can be adapted to use the invention.

FIG. 1 illustrates the usual components of a gas chromatograph including a source 2 of pressurized carrier gas, an injector 4 for introducing a sample of a mixture of gases into the stream of carrier gas flowing in a tube 6, a column 8 that causes the different gases of a sample mixture to elute from it one after the other, and a thermal conductivity cell 10 of the type described in U.S. Pat. No. 4,254,654 and sold by Hewlett-Packard Company under Accessory No. 19302A or Part. No. 19302-60530. The cell has a cavity 10' with a filament F mounted therein. The cavity 10' and the various passageways connecting thereto are molded in the interior surface of a ceramic wafer 11 that is covered by a wafer 11'. The wafers are embedded in a metal block 12 which is maintained at a desired temperature by any suitable means, such as a block temperature control 14, a resistance 16 embedded in the block, and a temperature sensing device 17 also embedded in the block.

Figure 1A:
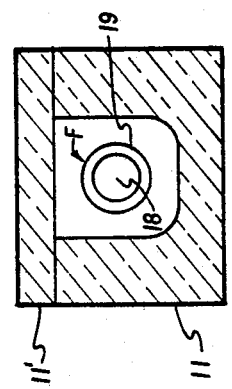
FIG. 1A illustrates a cross-section of the cavity of one type of thermal conductivity cell.

A filament F is mounted in the cavity 10' which, as illustrated in FIG. 1A, has a generally rectangular cross-section in a plane perpendicular to the filament F. In the acutal cell identified above, the filament F is made of tungsten wires having a diameter of 0.0005", a length of 12 mm. and a tungsten oxide coating 19 of at least $10 \times 10^{-6}$" in thickness. The length of the cavity 10' is slightly greater than 12 mm., its depth is 0.90 mm. and its width is 0.83 mm. The ends of the filament F are connected to a driver 20 which supplies an output signal indicative of the changes in the resistance or temperature of the filament to a synchronous detector 22, and its output is connected to a display device 23. As can be seen, the carrier gas and any sample gas present therein are conducted from the column 8 to a port 24 at one end of the cavity 10' by a passageway 25 formed in the metal block 12, the wafer 11' and the wafer 11. Reference gas, usually carrier gas, is supplied to a port 26 at the other end of the cavity 10' from a pressurized source 28 via a passageway 29 in the metal block 12, the wafer 11' and the wafer 11.

As more fully explained in the patent referred to above and in another U.S. Pat. No. 4,185,490, the carrier gas and any sample gas it contains is made to flow through the cavity 10' in one direction during spaced periods of time and reference gas is made to flow in the other direction through the cavity 10' during the intervening periods. One way of effecting this switching action is by respectively connecting tubes 30 and 32 between extensions of the passageways 25 and 29 and opposite sides of a stator 34 of a rotary valve 36. The rotor 38 has a 180° groove 40 in its outer periphery that lies in a radial plane and is rotated by a motor, not shown. The groove 40 is connected by a radial passageway 42 to an axial passageway 44 which is connected via a tube 45 to a source 46 of pressurized switching gas, which is usually carrier gas. A vent V is respectively connected by passageways 48 and 50 to points on the passageways 25 and 29 that are respectively intermediate the rotary valve 34 and the ports 24 and 26. As the rotor 38 turns at approximately ten revolutions a second, the carrier gas and reference gas alternately flow through the cavity 10' as desired. During one half-cycle, the signal from the driver 20 is due to carrier gas and any sample gas within the cavity 10', and during the next half-cycle, the signal from the driver 20 is due to reference gas flowing through the cavity 10'. An alternating current voltage corresponding to the frequency of rotation of the rotor 38 derived in any suitable manner and conveyed to the synchronous detector 22 which outputs a signal corresponding to the difference between a signal from the driver 20 that occurs when carrier and sample gas are flowing through the cavity 10' and the signal that occurs when reference gas is flowing through the cavity 10'. The signal from the synchronous detector 22 is conveyed to any suitable display means 52.

Reference is now made to the graphs of FIG. 2 in which the ordinate represents thermal conductivity and the abscissa represents the percent of sample gas contained in the carrier gas. The origin is the thermal conductivity of pure carrier gas, such as helium, the values above the origin occur when the mixture of carrier gas and sample gas has greater thermal conductivity than the carrier gas alone, and the values below the origin occur when the mixture of carrier gas and sample gas has less thermal conductivity than the carrier gas alone. Curve 54 is typical of the thermal conductivity of mixtures of carrier gas and all sample gas except hydrogen and shows that the thermal conductivity is reduced as the concentration of sample gas is increased. Because the concentration of a sample gas eluting from the column 8 has a Gaussian distribution, a chromatogram presented by the display device 23 for gases other than hydrogen appears as illustrated in FIG. 3A.

In view of the fact that the thermal conductivity of hydrogen is greater than that of the carrier gases usually employed, one would expect that a sample of hydrogen would increase the thermal conductivity of a carrier gas when it is mixed therewith, but when the temperature of the mixture is below a given value, the thermal conductivity of the mixture decreases to a minimum value M and then increases so as to cross through the thermal conductivity of the carrier gas alone at the point X' as indicated by the dashed curve 56. For even lower temperatures of the mixture, the thermal conductivity varies in a similar manner as illustrated by the curve 58 wherein the minimum value M' and the point X where it equals the thermal conductivity of the carrier gas occur at respectively higher concentrations.

Chromatograms for the low percentages of hydrogen less than those corresponding to the minimum values M and M' produce a normal chromatogram such as that of FIG. 3A. Whereas this may be of some use, it is subject to noise because the slight difference in the thermal conductivities of a mixture of hydrogen and carrier gas and carrier gas alone produces a small signal. If the maximum concentration of a hydrogen sample is between that of a minimum such as M and the crossover such as X, the chromatogram has a trough T in it as illustrated in FIG. 3B. The trough T deepens as the maximum concentration approaches that of the crossover such as X, and if the concentration is the same as at X, the trough goes to the baseline as illustrated at T' in FIG. 3C. If the maximum concentration of the hyrogen sample is greater than the concentration at crossover, the trough is seen to extend into the negative region as illustrated at T" of FIG. 3D. Chromatograms having a trough such as illustrated in FIGS. 3B through 3D are not generally useable and could only be made so by sophisticated integration means. Even so, the signal-to-noise ratio for low concentrations of hydrogen would be poor.

Another factor that prevents the production of reliable chromatograms for small concentrations of hydrogen in the carrier gas is the catalytic disassociation previously referred to. Whereas oxide coatings have been used in the past for the purpose of slowing down the oxidation of the filament wire, they now must be sufficiently thick to cover most of the sites where catalytic disassociation can take place. A tungsten oxide coating of at least $10 \times 10^{-6}$" is deemed satisfactory.

In accordance with this invention, the temperature of the filament F and the walls of the cavity 10' must be such as to make the average thermal conductivity of the mixture of hydrogen gas and carrier gas within the cavity 10' always greater than that of the carrier gas alone as illustrated by the curve 60. Any chromatograms produced will not have troughs and will be entirely on the negative side of the baseline as indicated in FIG. 3E so that they are all useful and there is no range of hydrogen concentration that cannot be successfully chromatographed. Furthermore, because the curve 60 is much farther from the abscissa for low concentrations of hydrogen, the sensitivity is greatly increased. In order to determine when the temperature of the filament F and the block 12 are such as to produce the desired operation secured by the invention, it is only necessary to observe chromatograms produced as the concentration of hydrogen is increased from zero to 20%. If a trough appears in any chromatograms, the invention is not being used.

In order to increase the sensitivity of the detector, the difference between the temperatures of the filament and the block should be as large as possible.

For the Hewlett-Packard thermal conductivity cell previously referred to, good results were obtained with the filament F at a temperature of 450° C. and the block 12 at a temperature of 200° C. It is quite possible that detectors of different design would require different temperatures. It is suggested therefore that the filament be established at 400° C. and the block at 100° C. If chromatograms with troughs are produced for any concentration of hydrogen below 20%, the filament temperature should be gradually increased until chromatograms without troughs are produced. If this does not occur by the time the filament has a temperature of 450° C. or the maximum temperature at which the filament is to be operated, the temperature of the block should be increased.

In the Hewlett-Packard cell, it is thought that the temperature of the filament is the most important factor and that the temperature gradient is flat most of the distance between the filament and the block and that it then falls off rapidly to the temperature of the block. Therefore, if the block is just outside the steep part of the temperature gradient, as it is in most designs, the filament used for different detectors can be the same.

What is claimed is:

1. Apparatus for detecting relative amounts of hydrogen in a mixture of gases, comprising
    a thermal conductivity detector having a block defining the walls of a cavity, a filament mounted in said cavity, said block also defining an input port near one end of said filament and an outlet port near the other end of said filament, whereby gas injected into said input port passes between the filament and the walls of said cavity and out the outlet port,
    output signal means coupled to said filament for producing an electrical signal indicative of the thermal conductivity of the gas in said cavity,
    a gas chromatographic column having one end coupled to said input port and an injector mounted so as to introduce a sample mixture of gases into a stream of helium that can flow into said input port, when a source of helium is coupled thereto,
    means for establishing said filament at a temperature in excess of 400° C. and means for establishing the temperature of said block at a lower temperature such that said output signal means produces a signal of one polarity for all concentrations of hydrogen.

2. Apparatus as set forth in claim 1 wherein said filament is passivated so that sites at which hydrogen can undergo catalytic disassociation are blocked.

3. A method for detecting the relative amount of hydrogen in a gaseous mixture, comprising
    introducing the mixture containing hydrogen into a stream of carrier gas before it enters a thermal conductivity detector, and
    establishing the temperature of the gases within the thermal conductivity detector at a value such that they exhibit a thermal conductivity greater than helium for any concentration of hydrogen.

4. Apparatus as set forth in claim 1 wherein said filament has an oxide coating that is at least $10 \times 10^{-6}$ inches thick.

5. Apparatus for detecting relative amounts of hydrogen in a mixture of gases, comprising
    a thermal conductivity detector having a block defining the walls of a cavity, a filament mounted in said cavity, said block also defining an input port near one end of said filament and an outlet port near the other end of said filament, whereby gas injected into said input port passes between the filament and the walls of said cavity and out the outlet port,
    output signal means coupled to said filament for producing an electrical signal indicative of the thermal conductivity of the gas in said cavity,
    a gas chromatographic column having one end coupled to said input port and an injector mounted so as to introduce a sample mixture of gases into a stream of helium that can flow into said input port, when a source of helium is coupled thereto, and
    means for establishing the temperature of said filament and said block, the temperature of the former being greater than the temperature of the latter and said temperatures being such that said output signal means produces a signal of one polarity with respect to the value of the signal when only helium is present in the cavity of the detector.

6. Apparatus as set forth in claim 5 wherein the filament is passivated with an oxide coating that is at least $10 \times 10^{-6}$ inches thick.

7. Apparatus for detecting relative amounts of deuterium in a mixture of gases, comprising
    a thermal conductivity detector having a block defining the walls of a cavity, a filament mounted in said cavity, said block also defining an input port near one end of said filament and an outlet port near the other end of said filament, whereby gas injected into said input port passes between the filament and the walls of said cavity and out the outlet port,
    output signal means coupled to said filament for producing an electrical signal indicative of the thermal conductivity of the gas in said cavity,
    a gas chromatographic column having one end coupled to said input port and an injector mounted so as to introduce a sample mixture of gases into a stream of helium that can flow into said input port, when a source of helium is coupled thereto, means for establishing the temperature of said filament and said block the temperature of the former being greater than the temperature of the latter and said temperatures being such that said output signal means produces a signal of one polarity with respect to the value of the signal when only deuterium is present in the cavity of the detector.

8. Apparatus as set forth in claim 7 wherein the filament is passivated with an oxide coating that is at least $10 \times 10^{-6}$ inches thick.

9. A method for detecting the relative amount of hydrogen in a gaseous mixture, comprising
passing a stream of helium through a thermal conductivity detector,
introducing a sample of the mixture into the stream of helium before it enters the detector, and
establishing the temperature of the gases within the detector at such a value that the chromatogram produced by the detector for hydrogen is a single peaked wave for any concentration thereof.

10. A method for detecting the relative amount of deuterium in a gaseous mixture, comprising
passing a stream of helium through a thermal conductivity detector,
introducing a sample of the mixture into the stream of helium before it enters the detector, and
establishing the temperature of the gases within the detector at such a value that the chromatogram produced by the detector for deuterium is a single peaked wave for any concentration thereof.

11. A method for detecting the relative amount of hydrogen in a gaseous mixture, comprising
passing a stream of helium through a thermal conductivity detector,
introducing a sample of the mixture into the stream of helium before it enters the detector, and
establishing the temperature of the gases within the detector at a value such that they exhibit a thermal conductivity greater than that of the helium within the detector for any concentration of hydrogen.

12. A method for detecting the relative amount of deuterium in a gaseous mixture, comprising
passing a stream of helium through a thermal conductivity detector,
introducing a sample of the mixture into the stream of helium before it enters the detector, and
establishing the temperature of the gases within the detector at a value such that they exhibit a thermal conductivity greater than that of the helium within the detector for any concentration of deuterium.

* * * * *